US012672775B2

(12) United States Patent
Afek et al.

(10) Patent No.: US 12,672,775 B2
(45) Date of Patent: Jul. 7, 2026

(54) ACCOMMODATION TRACKING BASED ON RETINAL-IMAGING

(71) Applicant: Apple Inc., Cupertino, CA (US)

(72) Inventors: Itai Afek, Kfar Sava (IL); Ariel Lipson, Tel Aviv (IL); Roei Remez, Tel Aviv (IL)

(73) Assignee: Apple Inc., Cupertino, CA (US)

( * ) Notice: Subject to any disclaimer, the term of this patent is extended or adjusted under 35 U.S.C. 154(b) by 563 days.

(21) Appl. No.: 18/118,936

(22) Filed: Mar. 8, 2023

(65) Prior Publication Data

US 2023/0309824 A1      Oct. 5, 2023

Related U.S. Application Data

(60) Provisional application No. 63/317,758, filed on Mar. 8, 2022.

(51) Int. Cl.
| | |
|---|---|
| *A61B 3/113* | (2006.01) |
| *G06T 7/73* | (2017.01) |
| *A61B 3/00* | (2006.01) |

(52) U.S. Cl.
CPC ............... *A61B 3/113* (2013.01); *G06T 7/73* (2017.01); *A61B 3/0025* (2013.01)

(58) Field of Classification Search
CPC ......... A61B 3/113; A61B 3/0025; G06T 7/73; G02B 27/0093; G06F 3/013
USPC ....................................................... 351/210
See application file for complete search history.

(56) References Cited

U.S. PATENT DOCUMENTS

| | | | | |
|---|---|---|---|---|
| 10,452,138 | B1 * | 10/2019 | Sharma .............. | G02B 27/0093 |
| 10,733,439 | B1 | 8/2020 | Geng et al. | |
| 10,778,954 | B1 | 9/2020 | Mercier et al. | |
| 2016/0081547 | A1 * | 3/2016 | Gramatikov ........... | G01N 21/23 |
| | | | | 356/369 |
| 2018/0084232 | A1 | 3/2018 | Belenkii et al. | |
| 2018/0136486 | A1 | 5/2018 | Macnamara et al. | |
| 2018/0292896 | A1 * | 10/2018 | Hicks ...................... | G06F 3/013 |
| 2020/0159030 | A1 * | 5/2020 | Ayres ................... | G02B 6/4215 |
| 2021/0034149 | A1 * | 2/2021 | Lin ......................... | G06T 7/292 |

(Continued)

FOREIGN PATENT DOCUMENTS

WO        2020/141537 A1      7/2020

OTHER PUBLICATIONS

European Patent Office (ISA/EP), International Search Report and Written Opinion of the International Searching Authority, International Application No. PCT/US2023/013754, 18 pages, Jun. 12, 2023.

*Primary Examiner* — Mohammed A Hasan
(74) *Attorney, Agent, or Firm* — Thompson Hine LLP

(57) ABSTRACT

Various implementations disclosed herein include devices, systems, and methods that track an eye characteristic (e.g., gaze direction, eye orientation, etc.). For example, an example process may include producing light that reflects off a retina of an eye, receiving an image of a portion of the retina from an image sensor, the image corresponding to a plurality of reflections of the light scattered from the retina of the eye, obtaining a representation of the eye corresponding to a first accommodative state, the representation representing at least some of the portion of the retina, and tracking an eye characteristic based on a comparison of the image of the portion of the retina with the representation of the eye.

26 Claims, 8 Drawing Sheets

(56)    References Cited

U.S. PATENT DOCUMENTS

| 2021/0045631 A1* | 2/2021 | Birkner | A61B 3/102 |
| 2021/0294106 A1 | 9/2021 | Meitav et al. | |

\* cited by examiner

500

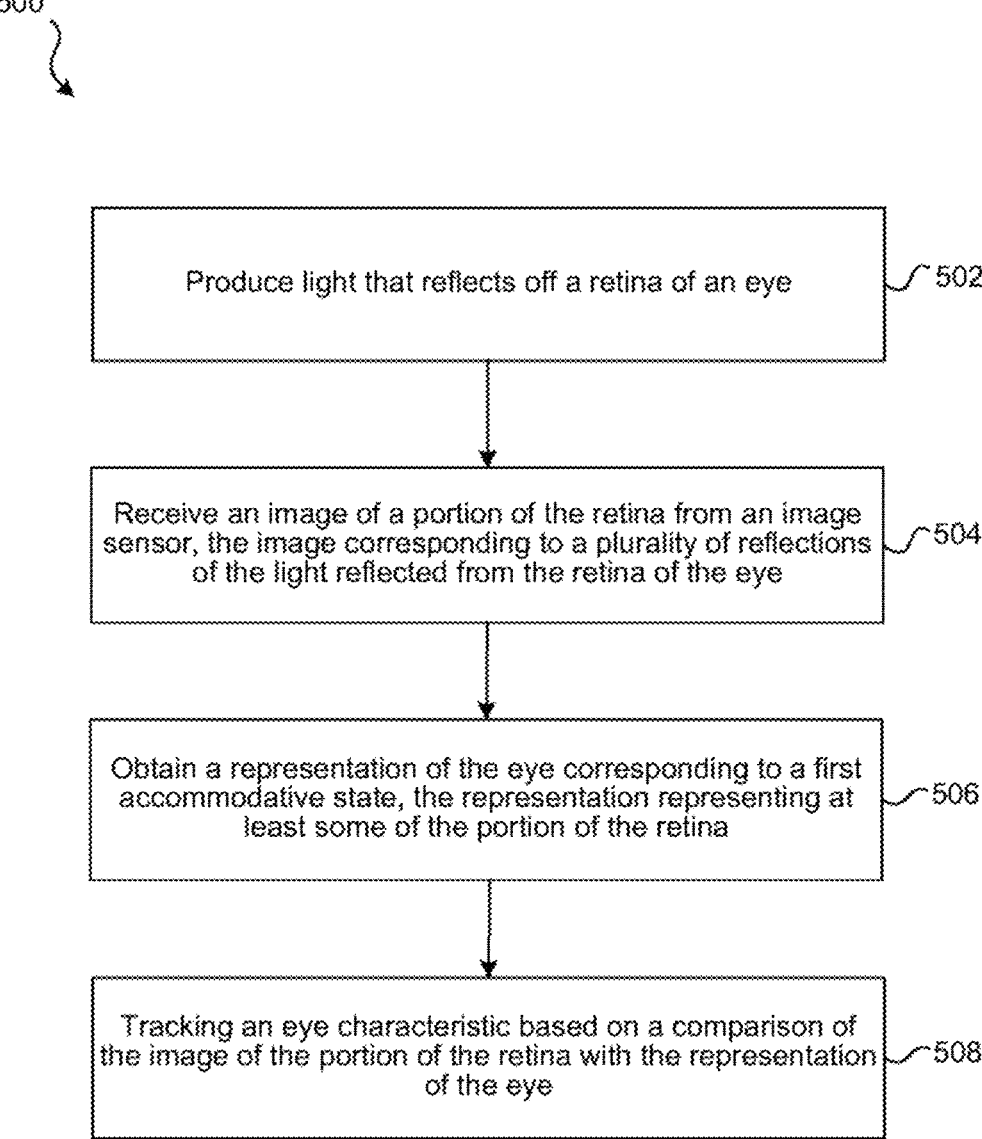

Produce light that reflects off a retina of an eye ⌒502

Receive an image of a portion of the retina from an image sensor, the image corresponding to a plurality of reflections of the light reflected from the retina of the eye ⌒504

Obtain a representation of the eye corresponding to a first accommodative state, the representation representing at least some of the portion of the retina ⌒506

Tracking an eye characteristic based on a comparison of the image of the portion of the retina with the representation of the eye ⌒508

FIG. 5

600

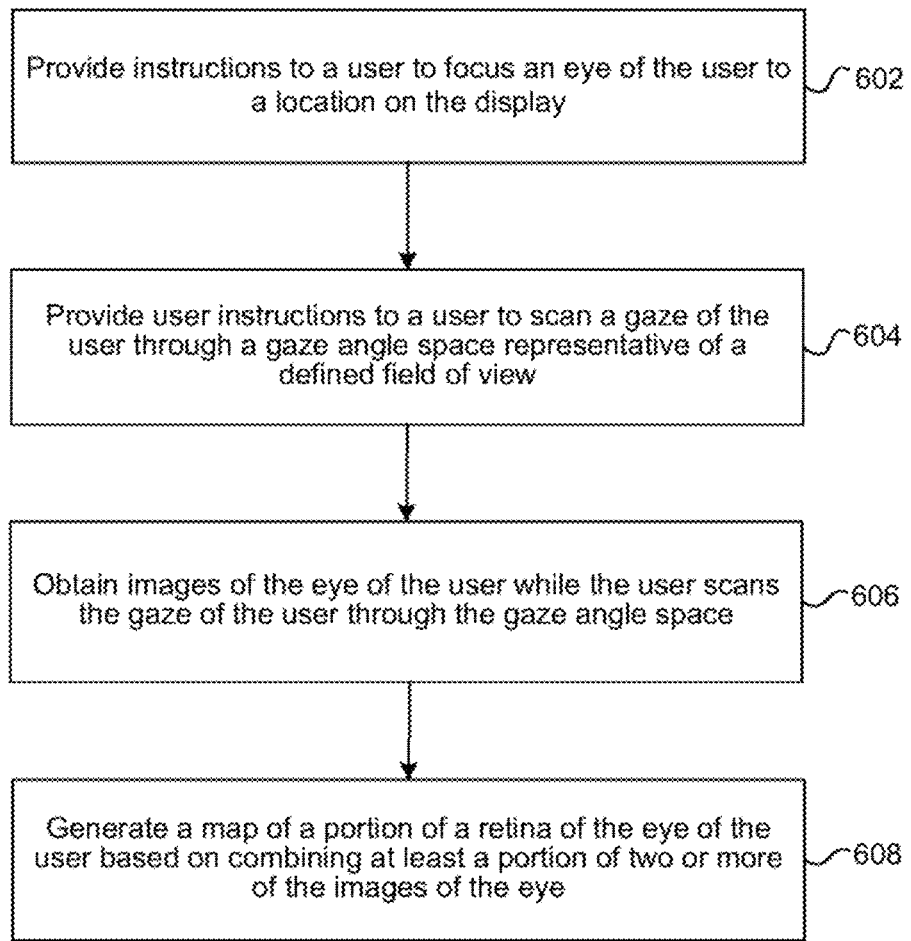

Provide instructions to a user to focus an eye of the user to a location on the display — 602

Provide user instructions to a user to scan a gaze of the user through a gaze angle space representative of a defined field of view — 604

Obtain images of the eye of the user while the user scans the gaze of the user through the gaze angle space — 606

Generate a map of a portion of a retina of the eye of the user based on combining at least a portion of two or more of the images of the eye — 608

FIG. 6

Device 700

Processing Unit(s) 702

Comm. Interface(s) 708

Display(s) 712

Memory 720

Operating System 730

Instruction Set(s) 740

Eye Representation Instruction Set 742

Eye Characteristic Tracking Instruction Set 744

704

I/O Device(s) & Sensor(s) 706

Programming Interface(s) 710

Image Sensor System(s) 714

ACCOMMODATION TRACKING BASED ON RETINAL-IMAGING

CROSS-REFERENCE TO RELATED APPLICATIONS

This application claims the benefit of U.S. Provisional Application No. 63/317,758 filed Mar. 8, 2022, entitled "ACCOMMODATION TRACKING BASED ON RETINAL-IMAGING," which is incorporated herein by this reference in its entirety.

TECHNICAL FIELD

The present disclosure generally relates to electronic devices, and in particular, to systems, methods, and devices for tracking an eye characteristic of users of electronic devices.

BACKGROUND

Existing eye-tracking techniques analyze glints that are reflected off of a user's eye and captured via an image sensor. Some head mounted systems may include eye-tracking techniques to analyze glint's using light projected from light sources located at an edge of a device (e.g., the frame of a pair of glasses). The eye-tracking system may lack accuracy on determining a depth of the viewer's gaze and be able to track the user's gaze depth in real-time. Thus, it may be desirable to provide a means of efficiently determining precisely which part of the scene (which distance, or "depth") the user is concentrated on for assessing an eye characteristic (e.g., gaze direction, eye orientation, identifying an iris of the eye, etc.) for head mountable systems.

SUMMARY

Various implementations disclosed herein include devices, systems, and methods that determines and tracks an eye characteristic (e.g., eye accommodation distance or depth) based on retinal imaging. Changes in eye accommodation induces two effects in the retinal image—scaling and defocus. In some aspects, a method acquires a retinal image, obtains an enrollment image, and determines user accommodation with respect to the enrollment image based on blurring (e.g., Point Spread Function (PSF)) and/or geometric scaling. Accommodation may be used to improve eye tracking and enhance an extended reality (XR) experience by enabling determination (with increased accuracy) of which part of the scene (e.g., which depth) the user is concentrated on and how well the user accommodates. Additionally, tracking accommodation can be used to better understand the user's precise behavior in real-time and adjust the XR experience accordingly. In some aspects, tracking accommodation can be used to adjust the perceived depth of content (e.g., virtual content) to the depth towards which the user is currently accommodated.

In general, one innovative aspect of the subject matter described in this specification can be embodied in methods that include the actions of, at an electronic device having a processor, producing light that reflects off a retina of an eye, receiving an image of a portion of the retina from an image sensor, the image corresponding to a plurality of reflections of the light scattered from the retina of the eye, obtaining a representation of the eye corresponding to a first accommodative state, the representation representing at least some of the portion of the retina, and tracking an eye characteristic based on a comparison of the image of the portion of the retina with the representation of the eye.

These and other embodiments can each optionally include one or more of the following features.

In some aspects, the representation of the eye includes a map of the at least some of the portion of the retina.

In some aspects, generating the map of the at least some of the portion of the retina includes obtaining enrollment images of the eye of a user while the user (i) accommodates the eye to an enrollment depth, and (ii) scans through a gaze angle space representative of a defined field of view, and generating the map of the at least some of the portion of the retina based on combining at least a portion of two or more of the enrollment images of the eye.

In some aspects, tracking the eye characteristic based on the comparison of the image of the portion of the retina with the representation of the eye includes estimating a degree of defocus of a feature. In some aspects, estimating the degree of defocus of the feature is based on focus pixels.

In some aspects, tracking the eye characteristic based on the comparison of the image of the portion of the retina with the representation of the eye includes sharpening the quality of the image of the portion of the retina, and determining an amount of defocus based on a lens movement required to sharpen the quality of the image of the portion of the retina.

In some aspects, tracking the eye characteristic based on the comparison of the image of the portion of the retina with the representation of the eye includes comparing a difference of a first feature width of the image of the portion of the retina with a second feature width of the representation of the eye to a threshold.

In some aspects, tracking the eye characteristic based on the comparison of the image of the portion of the retina with the representation of the eye is tracked at a same time the image of the portion of the retina is received.

In some aspects, the light is infrared (IR) light. In some aspects, the electronic device is a head-mounted device (HMD). In some aspects, the HMD includes a waveguide.

In general, one innovative aspect of the subject matter described in this specification can be embodied in methods that include the actions of, at an electronic device having a processor and a display, providing user instructions to a user to focus an eye of the user to a location on the display, and scan a gaze of the user through a gaze angle space representative of a defined field of view. The action further include obtaining images of the eye of the user while the user scans the gaze of the user through the gaze angle space, and generating a map of a portion of a retina of the eye of the user based on combining at least a portion of two or more of the images of the eye.

These and other embodiments can each optionally include one or more of the following features.

In some aspects, the actions further include determining enrollment data based on the map of the portion of the retina, and tracking the gaze of the user based on the enrollment data.

In some aspects, the actions further include determining a representation of the eye corresponding to a first accommodative state based on the generated map.

In some aspects, the actions further include producing light that reflects off the retina of the eye, receiving an image of a portion of the retina from an image sensor, the image corresponding to a plurality of reflections of the light scattered from the retina of the eye, and tracking an eye characteristic based on a comparison of the image of the portion of the retina with the generated map of the portion of the retina of the eye.

In some aspects, tracking the eye characteristic based on the comparison of the image of the portion of the retina with the representation of the eye includes estimating a degree of defocus of a feature.

In some aspects, estimating the degree of defocus of the feature is based on focus pixels.

In some aspects, tracking the eye characteristic based on the comparison of the image of the portion of the retina with the representation of the eye includes sharpening the quality of the image of the portion of the retina, and determining an amount of defocus based on a lens movement required to sharpen the quality of the image of the portion of the retina.

In some aspects, tracking the eye characteristic based on the comparison of the image of the portion of the retina with the representation of the eye includes comparing a difference of a first feature width of the image of the portion of the retina with a second feature width of the representation of the eye to a threshold.

In some aspects, tracking the eye characteristic based on the comparison of the image of the portion of the retina with the representation of the eye is tracked at a same time the image of the portion of the retina is received.

In some aspects, the user instructions include a visual notification presented on the display of the electronic device, an audio notification provided by a speaker of the electronic device, or a combination thereof.

In accordance with some implementations, a non-transitory computer readable storage medium has stored therein instructions that are computer-executable to perform or cause performance of any of the methods described herein. In accordance with some implementations, a device includes one or more processors, a non-transitory memory, and one or more programs; the one or more programs are stored in the non-transitory memory and configured to be executed by the one or more processors and the one or more programs include instructions for performing or causing performance of any of the methods described herein.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

FIG. 5 is a flowchart representation of a method for tracking an eye characteristic in accordance with some implementations.

FIG. 6 is a flowchart representation of a method for an enrollment process for tracking an eye characteristic in accordance with some implementations.

Figure 1:
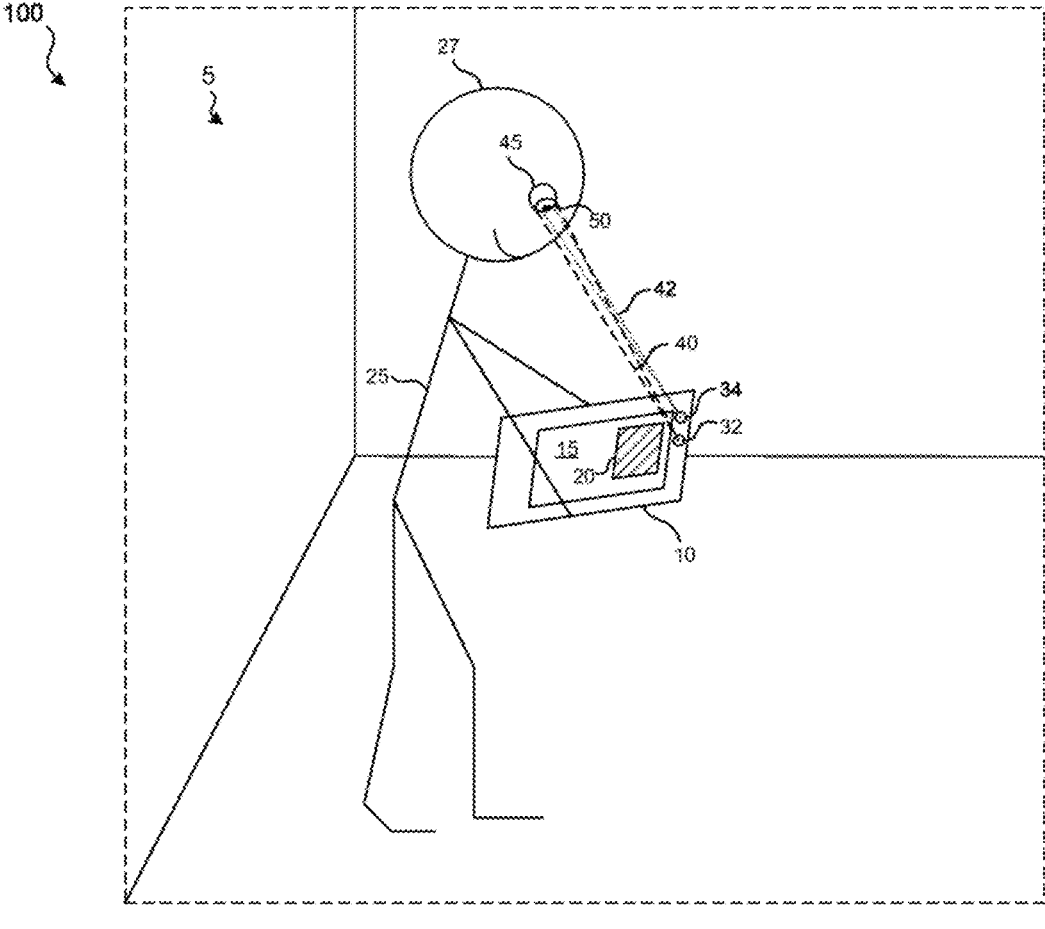
FIG. 1 illustrates a device displaying content and obtaining physiological data from a user according to some implementations.

In accordance with common practice the various features illustrated in the drawings may not be drawn to scale.

Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects or variants do not include all of the specific details described herein. Moreover, well-known systems, methods, components, devices and circuits have not been described in exhaustive detail so as not to obscure more pertinent aspects of the example implementations described herein.

FIG. 1 illustrates an example environment 100 of a real-world environment 5 (e.g., a room) including a device 10 with a display 15. In some implementations, the device 10 displays content 20 to a user 25. For example, content 20 may be a button, a user interface icon, a text box, a graphic, an avatar of the user or another user, etc. In some implementations, the content 20 can occupy the entire display area of display 15.

The device 10 obtains image data, motion data, and/or physiological data (e.g., pupillary data, facial feature data, etc.) from the user 25 via one or more sensors (e.g., sensor 32). For example, the device 10 obtains eye gaze characteristic data 40 via sensor 32. Additionally, the device 10 includes a light source 34 (e.g., a light-emitting diode (LED)) that may be used to illuminate specular and diffusive parts of the eye 45 of the user 25 via light rays 42 (e.g., infrared (IR) light).

While this example and other examples discussed herein illustrate a single device 10 in a real-world environment 5, the techniques disclosed herein are applicable to multiple devices as well as to other real-world environments. For example, the functions of device 10 may be performed by multiple devices, with the sensor 32 and light source 34 on each respective device, or divided among them in any combination.

In some implementations, as illustrated in FIG. 1, the device 10 is a handheld electronic device (e.g., a smartphone or a tablet). In some implementations the device 10 is a laptop computer or a desktop computer. In some implementations, the device 10 has a touchpad and, in some implementations, the device 10 has a touch-sensitive display (also known as a "touch screen" or "touch screen display"). In some implementations, the device 10 is a wearable device such as a head-mounted device (HMD).

In some implementations, the device 10 includes an eye-tracking system for detecting eye position and eye movements via eye gaze characteristic data 40. For example, an eye-tracking system may include one or more IR LEDs (e.g., light source 34), an eye tracking camera (e.g., near-IR (NIR) camera), and an illumination source (e.g., an NIR light source) that emits light (e.g., NIR light) towards the eyes of the user 25. Moreover, the illumination source of the device 10 may emit NIR light to illuminate the eyes of the user 25 and the NIR camera may capture images of the eyes of the user 25. In some implementations, images captured by the eye-tracking system may be analyzed to detect position and movements of the eyes of the user 25, or to detect other information about the eyes such as color, shape, state (e.g., wide open, squinting, etc.), pupil dilation, or pupil diameter. Moreover, the point of gaze estimated from the eye tracking images may enable gaze-based interaction with content shown on the near-eye display of the device 10.

In some implementations, the device 10 has a graphical user interface (GUI), one or more processors, memory and one or more modules, programs or sets of instructions stored in the memory for performing multiple functions. In some implementations, the user 25 interacts with the GUI through finger contacts and gestures on the touch-sensitive surface. In some implementations, the functions include image editing, drawing, presenting, word processing, website creating, disk authoring, spreadsheet making, game playing, telephoning, video conferencing, e-mailing, instant messaging, workout support, digital photographing, digital videoing, web browsing, digital music playing, and/or digital video playing. Executable instructions for performing these functions may be included in a computer readable storage medium or other computer program product configured for execution by one or more processors.

In some implementations, one or both eyes 45 of the user 25, including one or both pupils 50 of the user 25 present physiological data in the form of a pupillary response (e.g., eye gaze characteristic data 40) detected from a glint analysis. The pupillary response of the user 25 may result in a varying of the size or diameter of the pupil 50, via the optic and oculomotor cranial nerve. For example, the pupillary response may include a constriction response (miosis), e.g., a narrowing of the pupil, or a dilation response (mydriasis), e.g., a widening of the pupil. In some implementations, the device 10 may detect patterns of physiological data representing a time-varying pupil diameter.

Figure 2:
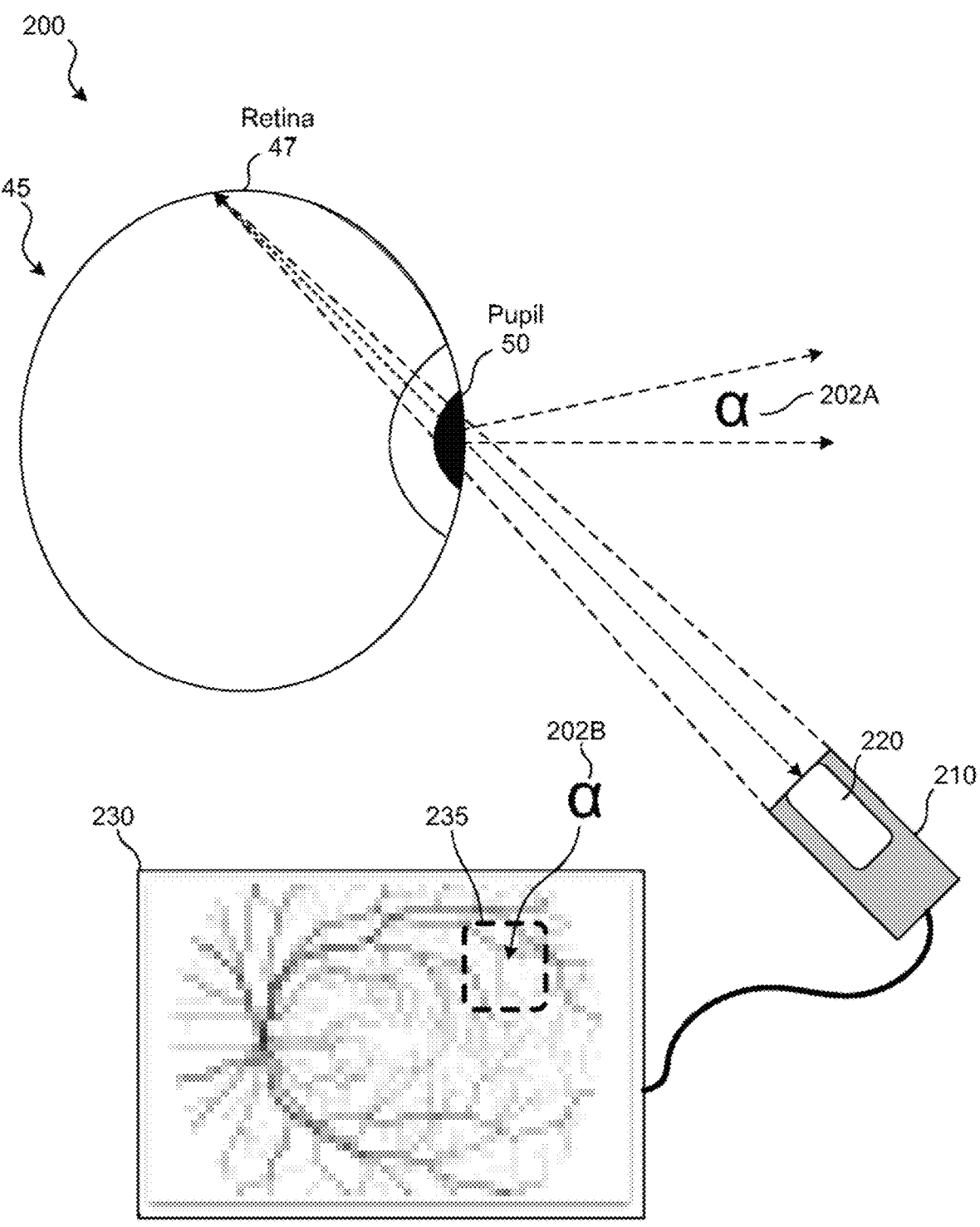
FIG. 2 illustrates an example eye-tracking system in accordance with some implementations.

FIG. 2 illustrates an example environment 200 of an eye-tracking system in accordance with some implementations. The eye-tracking system of example environment 200 uses a light source 210 such as a LED ring that produces IR light (e.g., light source 34 on device 10). Additionally, the eye-tracking system includes image sensor 220 (e.g., sensor 32 on device 10) to observe light scattered off of the retina 47 of the eye 45 in order to acquire an image 230 of the retina 47. As illustrated, the acquired image 230 provides a view of the blood vessels of the eye 45. Additionally, or alternatively, in some implementations, the acquired image may provide additional information other than blood vessels such as other detectable retinal features. In some implementations, as illustrated, the image sensor 220 is embedded within or in line with the light source 210 (e.g., an LED ring on an HMD). Additionally, or alternatively, in some implementations, the image sensor 220 and the light source are separated and/or are not in line. However, according to some aspects, the alignment of acquiring the retinal image scan of the retina 47 with the IR light produced by the light source 210 improves accuracy for determining an accommodation depth/distance of the eye 45.

In some implementations, as illustrated in FIG. 2, the light source 220 (e.g., an LED or the like), illuminates a surface of the retina 47 of the eye 45 of the user as the user is accommodating his or her sight (e.g., viewing angle α 202a). The image sensor 210 then acquires retina-based gaze tracking images of the retina 47 as the light is reflected off of a surface of the retina 47 (e.g., portion 235 of image 230 shows the location viewing angle α 202b associated with the viewing angle α 202a). For example, during an enrollment process, the user 25 may be instructed to focus his or her gaze to a particular location that is off in the distance of the display (e.g., focus at a location with that is 1.5 m away). For example, the particular location may be on the display 15 of the device 10. If the user 25 is wearing the device 10 on his or her head (e.g., an HMD), than the location may appear on the display at a very far away distance (e.g., stare off into a small point such that the gaze may be looking out into infinity). The light waves from the light source 210 are then reflected off of the retina of the eye 45 and detected by a detector (e.g., image sensor 220) to acquire image data of the retinal surface. The lens of the image sensor 220 may be focused to infinity such that when combined with the eye's optics the retinal surface is sharply imaged onto the image sensor (e.g., when the eye is focused to infinity, which is the default for relaxed, healthy eye).

In some aspects, the enrollment phase may further include providing instructions to the user to scan a gaze of the user through a gaze angle space representative of a defined field of view. For example, while a user is wearing the device on his or her head (e.g., an HMD), visual and/or audio notifications may be provided to the user to scan the horizon (e.g., detect the eye gaze as it is varied spatially, such as along the azimuth). If the user 25 is holding the device (e.g., a tablet) as illustrated in FIG. 1, then the user may be instructed to gaze at what appears to be a small point off in the distance in the content 20 of the display 15 of the device 10. In some implementations, the enrollment phase may further include obtaining images of the eye of the user (e.g., image 230 acquired from image sensor 210) while the user scans the gaze of the user through the gaze angle space (e.g., viewing angle α 202a). In some implementations, the enrollment phase may further include generating a map (e.g., an enrollment image) of a portion of a retina 47 of the eye 45 of the user based on combining (e.g., stitching) at least a portion of two or more of the images of the eye.

Figure 3:
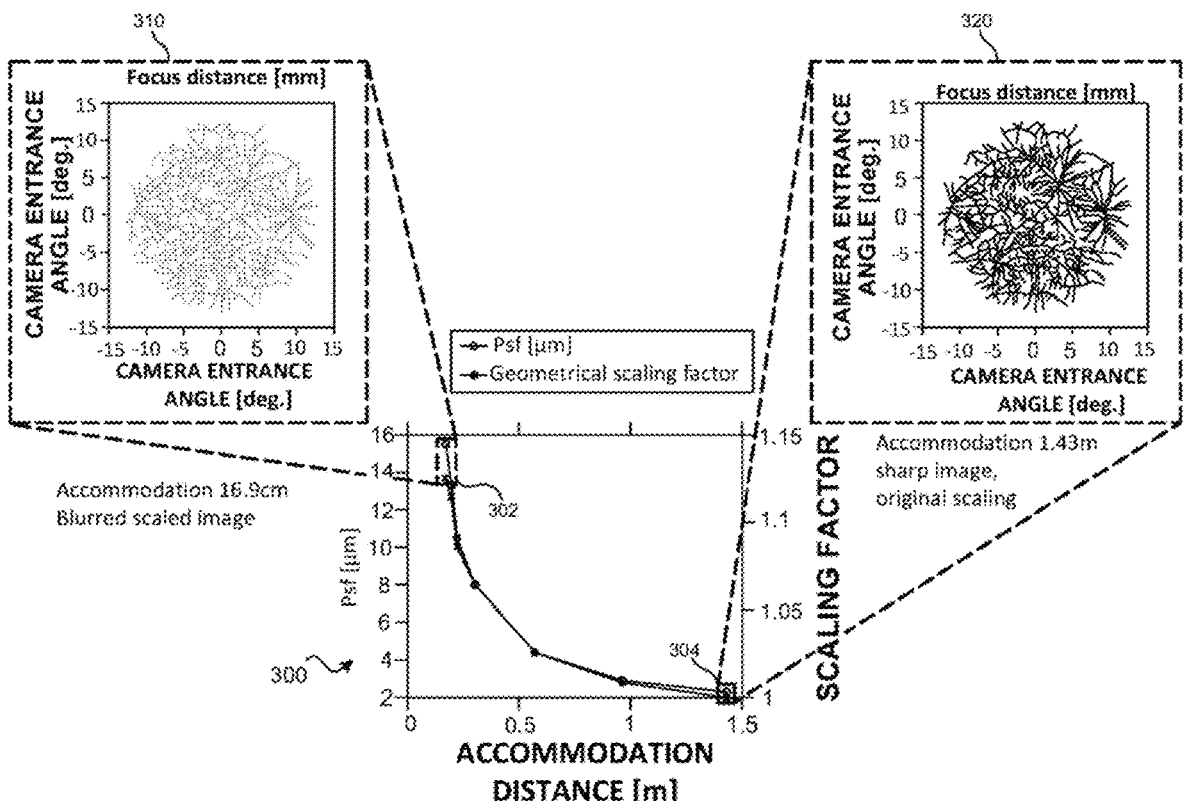
FIG. 3 illustrates an optical effect of user accommodation for an example eye-tracking system in accordance with some implementations.

FIG. 3 illustrates an optical effect of user accommodation for an example eye-tracking system in accordance with some implementations. In particular, according to an exemplary implementation, given a retinal image (e.g., real-time data) and corresponding enrollment image (e.g., a calibrated image acquired during an enrollment phase), the eye tracking system described herein can retrieve the user accommodation based on a determined point spread function (PSF) and geometric scaling as there is a 1:1 correspondence between scaling/defocus and eye accommodation.

In particular, FIG. 3 illustrates graph 300 that provides a visual for blurring (e.g., defocus) measured by a PSF. For example, the PSF is measured in micrometers (μm) for a range of 2 μm to 16 μm as an accommodation distance changes. The graph 300 further provides a visual for a scaling factor to apply geometric scaling that is affected by a change in eye accommodation. For example, the geometric scaling includes a factoring range from 1.0 to 1.15 as an accommodation distance changes. The graph further provides on the x-axis the accommodation distances measured in meters (m) for a range of 0.0 m to 1.5 m. For example, for blurred scaled image at a first accommodation distance (e.g., focus distance 169 mm as illustrated by image 310), the PSF and the scaling factor are shown at area 302. Additionally, for example, for a sharp image with original scaling (e.g., scaling at 1.0), at a second accommodation distance (e.g., focus distance 1,430 mm as illustrated by image 320), the PSF and the scaling factor are shown at area 304.

Figure 4:
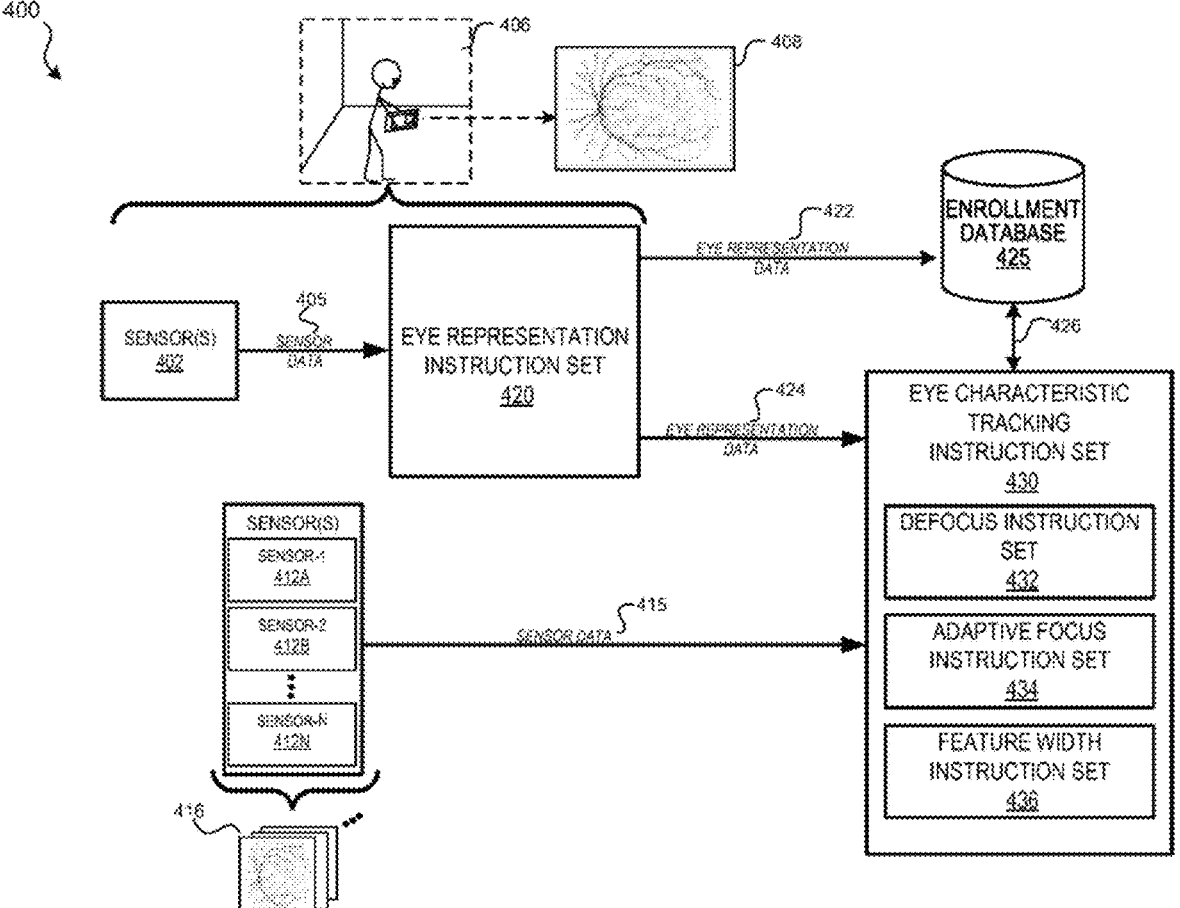
FIG. 4 illustrates a system flow diagram for tracking an eye characteristic in accordance with some implementations.

FIG. 4 is a system flow diagram of an example environment 400 in which a system can track eye characteristics according to some implementations. In some implementations, the system flow of the example environment 400 is performed on a device (e.g., device 10 of FIG. 1), such as a mobile device, desktop, laptop, or server device. The images of the example environment 400 can be displayed on a device (e.g., device 10 of FIG. 1) that has a screen for displaying images and/or a screen for viewing stereoscopic images such as a head-mounted device (HMD). In some implementations, the system flow of the example environment 400 is performed on processing logic, including hardware, firmware, software, or a combination thereof. In some implementations, the system flow of the example environment 400 is performed on a processor executing code stored in a non-transitory computer-readable medium (e.g., a memory).

In some implementations, the system flow of the example environment 400 includes an enrollment process for generating eye representation data and an eye characteristic tracking process. Alternatively, the example environment 400 may only include the eye characteristic tracking process and obtain the enrollment data from another source (e.g., previously stored enrollment data). In other words, the enrollment process may have already taken place such that the user's enrollment data is already provided because an enrollment process has already completed.

The system flow of the enrollment process of the example environment 400 acquires sensor data 405 (e.g., image data) from sensors 402 of a physical environment (e.g., the physical environment 5 of FIG. 1), and generates eye representation data 422, 424. For example, during an enrollment (or registration) phase, a representation or a map of the retina may be generated by having the user accommodate to an enrollment depth (e.g., infinity, 30 cm, 1 m, and the like), and scan through gaze angle space covering a desired field of view (e.g., varied spatially, such as along the azimuth). For example, a device may display a visual indicator (e.g., a small, highlighted dot) for the user to focus on in the distance (horizon). Then the device can provide a notification to the user to scan his or her view across the desired field of view. The notification could be a visual notification (e.g., a text block that instructs the user to scan the horizon and/or moving the visual indicator across the horizon for the user to follow). Additionally, or alternatively, the notification could be an audio notification (e.g., "now scan the horizon as you are looking out into the distance").

In an example implementation, the environment 400 includes an image composition pipeline that acquires or obtains data (e.g., image data from image source(s) such as sensors 402 and 412A-412N) of the physical environment. Example environment 400 is an example of acquiring image sensor data 405 (e.g., IR data from reflections of light) for the enrollment process and acquiring image sensor data 415 (e.g., IR data) for the eye characteristic tracking process for a plurality of image frames. For example, illustration 406 (e.g., example environment 100 of FIG. 1) represents a user acquiring image data 408 as the user scans his or her eye(s) 45 in a physical environment (e.g., the physical environment 5 of FIG. 1) during an enrollment process. Image(s) 416 represent a user acquiring image data as the user scans his or her eye(s) 45 in real-time (e.g., during an XR experience while wearing an HMD). The image sensor(s) 412A, 412B, through 412N (hereinafter referred to sensors 412) may include one or more images sensors for capturing image data of the eye, specifically the retina, based on reflected IR data.

In an example implementation, the environment 400 includes an eye representation instruction set 420 that is configured with instructions executable by a processor to generate eye representation data from sensor data. For example, the eye representation instruction set 420 acquires sensor data 405 from sensors 402 such as IR image data (e.g., image 408) of the eye 45 of the user 25. For example, instructions may be determined by the eye representation instruction set 420 to direct the user through an enrollment process. Those instructions may be provided to the user via audio and/or visual cues. The cues may include the instructional phrases such as "stare off into the distance at the dot" to have the user stare to a particular depth (e.g., infinity, 1 m, 30 cm, and the like), to capture the correct accommodation, and a cue to "now scan the horizon as you are looking out into the distance," etc. Additionally, or alternatively, visual icons (e.g., arrows) or images may be provided. The audio and/or visual cues provide the eye representation instruction set 420 with one or more images of the retina that provide a range of accommodation depth data. The eye representation instruction set 420 can store the eye representation data 422 in the enrollment database 425 to be later accessed by the eye characteristic tracking instruction set 430. Additionally, or alternatively, the eye representation instruction set 420 can send the eye representation data 424 directly to the eye characteristic tracking instruction set 430 to be used immediately (e.g., a new user that wants to engage in immediately with an application that utilizes an eye tracking system).

In an example implementation, the environment 400 includes an eye characteristic tracking instruction set 430 that is configured with instructions executable by a processor to track an eye characteristic (e.g., user accommodation distance via scaling and blurring) based on a comparison of the image of the portion of the retina with the representation of the eye. For example, the eye characteristic tracking instruction set 430 acquires sensor data 415 from sensors 412 (e.g., real-time image data of the eye, such as IR) of a user's eye in a physical environment (e.g., user 25 in the physical environment 5 of FIG. 1), acquires the eye representation data 424 from the eye representation instruction set 420 (or the eye representation data 426 from the enrollment database 425), and tracks an eye characteristic such as eye accommodation depth data.

In some implementations, the eye characteristic tracking instruction set 430 includes one or more instruction sets for tracking an eye characteristic based on a comparison of the image of the portion of the retina with the representation of the eye. In some implementations, tracking the eye characteristic is based on user accommodation distance determined via scaling and blurring. Several methods and or combinations of methods may be utilized to track an eye characteristic based on a comparison of the image of the portion of the retina with the representation of the eye.

In some implementations, a method may use 'focus pixels' by the defocus instruction set 432 to estimate the degree of defocus of a given feature. In an exemplary implementation, tracking the eye characteristic based on the comparison of the image of the portion of the retina with the representation of the eye includes estimating a degree of defocus of a feature. In some implementations, estimating the degree of defocus of the feature is based on focus pixels (e.g., an imaging technique to determine focus/blur).

Additionally, or alternatively, in some implementations, the eye characteristic tracking instruction set 430 may use adaptive focus via the adaptive focus instruction set 434 to sharpen the image and then determine the defocus by the amount of lens movement required. In some implementations, user accommodation is based on an adaptive focus technique to sharpen the image of the retina and then determine the defocus by the amount of lens movement required (e.g., the hardware of the camera, such as image sensor 220, adapts based on the acquired image data). In an exemplary implementation, tracking the eye characteristic based on the comparison of the image of the portion of the retina with the representation of the eye includes sharpening the quality of the image of the portion of the retina, and determining an amount of defocus based on a lens movement required to sharpen the quality of the image of the portion of the retina (e.g., adaptive focus).

Additionally, or alternatively, in some implementations, the eye characteristic tracking instruction set 430 method may use the feature width instruction set 436 to determine a comparison of a feature width at enrollment and in a given image (e.g., real time or acquired at a later time), such that the larger the width, the more the defocus. In an exemplary implementation, tracking the eye characteristic based on the comparison of the image of the portion of the retina with the representation of the eye includes comparing a difference of a first feature width of the image of the portion of the retina with a second feature width of the representation of the eye to a threshold (e.g., the larger the width, the more the defocus).

FIG. 5 is a flowchart illustrating an exemplary method 500. In some implementations, a device (e.g., device 10 of FIG. 1) performs the techniques of method 500 for tracking an eye characteristic of a user in accordance with some implementations. In some implementations, the techniques of method 500 are performed on a mobile device, desktop, laptop, HMD, or server device. In some implementations, the method 500 is performed on processing logic, including hardware, firmware, software, or a combination thereof. In some implementations, the method 500 is performed on a processor executing code stored in a non-transitory computer-readable medium (e.g., a memory). In an exemplary implementation, the techniques of method 500 are performed at an electronic device (e.g., an HMD) having a processor. In some implementations, the HMD includes a waveguide as at least a portion of the display.

At block 502, the method 500 produces light that reflects off a retina of an eye. For example, as illustrated in FIG. 2, the eye-tracking system of example environment 200 uses a light source 210 (such as a LED ring) that produces IR light and an image sensor 220 to observe light scattered off of a surface of the retina 47 of the eye 45 in order to acquire an image 230 of the retina 47.

In some implementations, the light is IR light. In some implementations, the light source is a LED. Alternatively, another type of light source may be used that sufficiently provides a retinal-based image when the light from the light source is projected onto the eye.

At block 504, the method 500 receives an image of a portion of the retina from an image sensor, the image corresponding to a plurality of reflections of the light scattered from the retina of the eye. For example, the sensor (e.g., image sensor 220) may be an IR image sensor/detector. For example, as illustrated in FIG. 2, the eye-tracking system of example environment 200 uses image sensor 220 to observe light scattered off of a surface of the retina 47 of the eye 45 in order to acquire an images of the retina 47 (e.g., image 230).

At block 506, the method 500 obtains a representation of the eye (e.g., an enrollment image/map) corresponding to a first accommodative state. The representation may represent at least some of the portion of the retina. For example, the representation may be a map of the retina generated by having the user accommodate to a particular depth (e.g., infinity, 30 cm, 1 m, etc.), and scan through gaze angle space representative of the full desired field of view (e.g., a registration of an enrollment process). The captured images from the enrollment phase may then be stitched together to form a map of the retina.

In some implementations, obtaining a representation of the eye is based on generating an enrollment image of the retina of the eye to be used with the eye tracking system (e.g., register a new user before using an eye tracking system). In an exemplary implementation, the representation of the eye includes a map of the at least some of the portion of the retina. In some implementations, generating the map of the at least some of the portion of the retina includes obtaining enrollment images of the eye of a user, and generating the map of the at least some of the portion of the retina based on combining (stitching) at least a portion of two or more of the enrollment images of the eye. In some implementations, obtaining enrollment images is performed while the user (i) accommodates the eye to a particular enrollment depth (e.g., infinity, 30 cm, 1 m, etc.), and (ii) scans through a gaze angle space representative of a defined field of view. For example, before the user can access/use a particular program on a device, the system performs a user registration process that includes capturing an enrollment image(s) of the retina that can be used during use of the program for eye tracking (e.g., a first time a new user uses an HMD).

At block 508, the method 500 tracking an eye characteristic based on a comparison of the image of the portion of the retina with the representation of the eye. In some implementations, tracking the eye characteristic is based on user accommodation distance determined via scaling and blurring. Several methods and or combinations of methods may be utilized to track an eye characteristic based on a comparison of the image of the portion of the retina with the representation of the eye. For example, in one implementation, a method may use 'focus pixels' to estimate the degree of defocus of a given feature. Additionally, or alternatively, in one implementation, a method may use adaptive focus to sharpen the image and then determine the defocus by the amount of lens movement required. Additionally, or alternatively, in one implementation, a method may use a comparison of a feature width at enrollment and in a given image (e.g., real time or acquired at a later time), such that the larger the width, the more the defocus.

In an exemplary implementation, tracking the eye characteristic based on the comparison of the image of the portion of the retina with the representation of the eye includes estimating a degree of defocus of a feature. In some implementations, estimating the degree of defocus of the feature is based on focus pixels (e.g., an imaging technique to determine focus/blur).

In some implementations, user accommodation is based on an adaptive focus technique to sharpen the image of the retina and then determine the defocus by the amount of lens movement required (e.g., the hardware of the camera, such as image sensor 220, adapts based on the acquired image data). In an exemplary implementation, tracking the eye characteristic based on the comparison of the image of the portion of the retina with the representation of the eye includes sharpening the quality of the image of the portion of the retina, and determining an amount of defocus based on a lens movement required to sharpen the quality of the image of the portion of the retina (e.g., adaptive focus).

In some implementations, a feature width of the user accommodation is compared between an enrollment image of the retina and another image of the retina (e.g., the more the width the more defocus). In an exemplary implementation, tracking the eye characteristic based on the comparison of the image of the portion of the retina with the representation of the eye includes comparing a difference of a first feature width of the image of the portion of the retina with a second feature width of the representation of the eye to a threshold (e.g., the larger the width, the more the defocus). In some implementations, an example threshold distance to use for a threshold comparison between the feature width at enrollment and in a given image may be based on a feature size difference in pixels that is larger than one pixel. Additionally, or alternatively, in some implementations, an example threshold distance to use for a threshold comparison between the feature width at enrollment and in a given image may be based on a size (e.g., in a number of pixels) of the defocus kernel needed to convert from enrollment image's to captured image's feature sizes and shape.

In some implementations, user accommodation is tracked in real-time. In an exemplary implementation, tracking the eye characteristic based on the comparison of the image of the portion of the retina with the representation of the eye is tracked at the same time (e.g., real-time) the image of the portion of the retina is received. For example, during the use of an application (e.g., an XR experience), eye tracking is performed in real-time, such as to initiate an action based on the real-time tracking of the user's eye(s) to enhance the XR experience.

In some implementations, tracking an eye characteristic based on a comparison of the image of the portion of the retina with the representation of the eye may include a biometric enrollment and tracking process, and/or used for biometric identification. For example, a biometric enrollment and tracking process may include an iris identification and/or iris recognition or tracking a retina ID based on retinal features. For example, iris recognition is an automated method of biometric identification that uses mathematical pattern-recognition techniques on video images of one or both of the irises of an individual's eyes, whose complex patterns are unique, stable, and can be seen from some distance.

In some implementations, tracking an eye characteristic based on a comparison of the image of the portion of the retina with the representation of the eye may be used for a gaze tracking refinement process. For example, if there is an object close-by and we know the user is accommodated at that object's distance and looking approximately (e.g., within a threshold distance) in that direction, it can be more precisely determined that the user is looking in the direction of the object.

In some implementations, the method 500 further includes determining an eye characteristic based on a determined location of user's accommodation depth. For example, the eye characteristic may include a gaze direction, eye orientation, or the like, for an eye-tracking system. For example, if the electronic device is an HMD, the eye-tracking system for the HMD can track gaze direction, eye orientation, etc. of a user.

In some implementations, determining an eye characteristic includes determining locations of multiple portions of the eye based on determining locations of accommodations depths based on several images of the retina as the user changes his or her gaze.

FIG. 6 is a flowchart illustrating an exemplary method 600. In some implementations, a device (e.g., device 10 of FIG. 1) performs the techniques of method 600 for tracking an eye characteristic of a user in accordance with some implementations. In some implementations, the techniques of method 600 are performed on a mobile device, desktop, laptop, HMD, or server device. In some implementations, the method 600 is performed on processing logic, including hardware, firmware, software, or a combination thereof. In some implementations, the method 600 is performed on a processor executing code stored in a non-transitory computer-readable medium (e.g., a memory). In an exemplary implementation, the techniques of method 600 are performed at an electronic device (e.g., an HMD) having a processor. In some implementations, the HMD includes a waveguide as at least a portion of the display.

At block 602, the method 600 provides user instructions to a user to focus an eye of the user to a location on the display, and then at block 604, the method 600 provides instructions to a user to scan a gaze of the user through a gaze angle space representative of a defined field of view. For example, during an enrollment (or registration) phase, a representation or a map of the retina may be generated by having the user accommodate to a particular known enrollment depth (e.g., infinity, 30 cm, 1 m, etc.), and scan through gaze angle space covering a desired field of view (e.g., varied spatially, such as along the azimuth).

In some implementations, the user instructions include a visual notification presented on the display of the electronic device, an audio notification provided by a speaker of the electronic device, or a combination thereof. For example, a device may display a visual indicator (e.g., a small, highlighted dot) for the user to focus on in the distance (horizon). Then the device can provide a notification to the user to scan his or her view across the desired field of view. The notification could be a visual notification (e.g., a text block that instructs the user to scan the horizon and/or moving the visual indicator across the horizon for the user to follow). Additionally, or alternatively, the notification could be an audio notification (e.g., "now scan the horizon as you are looking out into the distance").

At block 606, the method 600 obtains images of the eye of the user while the user scans the gaze of the user through the gaze angle space. For example, as illustrated in FIG. 2, the eye-tracking system of example environment 200 uses a light source 210 (such as a LED ring) that produces IR light and an image sensor 220 to observe light scattered off of a surface of the retina 47 of the eye 45 in order to acquire an image 230 of the retina 47. In some implementations, the light is IR light. In some implementations, the light source is a LED. Alternatively, another type of light source may be used that sufficiently provides a retinal-based image when the light from the light source is projected onto the eye. For example, the sensor (e.g., image sensor 220) may be an IR image sensor/detector. For example, as illustrated in FIG. 2, the eye-tracking system of example environment 200 uses image sensor 220 to observe light scattered off of a surface of the retina 47 of the eye 45 in order to acquire an images of the retina 47 (e.g., image 230).

At block 608, the method 600 obtains a representation of the eye (e.g., an enrollment image/map) corresponding to a first accommodative state. The representation may represent at least some of the portion of the retina. For example, the representation may be a map of the retina generated by having the user accommodate to a known enrollment depth (e.g., infinity, 30 cm, 1 m, etc.), and scan through gaze angle space representative of the full desired field of view (e.g., a registration of an enrollment process). The captured images from the enrollment phase may then be stitched together to form a map of the retina.

In some implementations, obtaining a representation of the eye is based on generating an enrollment image of the retina of the eye to be used with the eye tracking system (e.g., register a new user before using an eye tracking system). In an exemplary implementation, the representation of the eye includes a map of the at least some of the portion of the retina. In some implementations, generating the map of the at least some of the portion of the retina includes obtaining enrollment images of the eye of a user, and generating the map of the at least some of the portion of the retina based on combining (stitching) at least a portion of two or more of the enrollment images of the eye. In some implementations, obtaining enrollment images is performed while the user (i) accommodates the eye to a particular enrollment depth, and (ii) scans through a gaze angle space representative of a defined field of view. For example, before the user can access/use a particular program on a device, the system performs a user registration process that includes capturing an enrollment image(s) of the retina that can be used during use of the program for eye tracking (e.g., a first time a new user uses an HMD).

In some implementations, the method 600 further includes determining enrollment data based on the map of the portion of the retina, and tracking the gaze of the user based on the enrollment data. In some implementations, the method 600 further includes determining a representation of the eye (e.g., an enrollment image/map) corresponding to a first accommodative state based on the generated map.

In some implementations, the method 600 further includes producing light that reflects off the retina of the eye, receiving an image of a portion of the retina from an image sensor, the image corresponding to a plurality of reflections of the light scattered from the retina of the eye, and tracking an eye characteristic based on a comparison of the image of the portion of the retina with the representation of the eye. In some implementations, tracking the eye characteristic is based on user accommodation distance determined via scaling and blurring. Several methods and or combinations of methods may be utilized to track an eye characteristic based on a comparison of the image of the portion of the retina with the representation of the eye. For example, in one implementation, a method may use 'focus pixels' to estimate the degree of defocus of a given feature. Additionally, or alternatively, in one implementation, a method may use adaptive focus to sharpen the image and then determine the defocus by the amount of lens movement required. Additionally, or alternatively, in one implementation, a method may use a comparison of a feature width at enrollment and in a given image (e.g., real time or acquired at a later time), such that the larger the width, the more the defocus.

In an exemplary implementation, tracking the eye characteristic based on the comparison of the image of the portion of the retina with the representation of the eye includes estimating a degree of defocus of a feature. In some implementations, estimating the degree of defocus of the feature is based on focus pixels (e.g., an imaging technique to determine focus/blur).

In some implementations, user accommodation is based on an adaptive focus technique to sharpen the image of the retina and then determine the defocus by the amount of lens movement required (e.g., the hardware of the camera, such as image sensor 220, adapts based on the acquired image data). In an exemplary implementation, tracking the eye characteristic based on the comparison of the image of the portion of the retina with the representation of the eye includes sharpening the quality of the image of the portion of the retina, and determining an amount of defocus based on a lens movement required to sharpen the quality of the image of the portion of the retina (e.g., adaptive focus).

In some implementations, a feature width of the user accommodation is compared between an enrollment image of the retina and another image of the retina (e.g., the more the width the more defocus). In an exemplary implementation, tracking the eye characteristic based on the comparison of the image of the portion of the retina with the representation of the eye includes comparing a difference of a first feature width of the image of the portion of the retina with a second feature width of the representation of the eye to a threshold (e.g., the larger the width, the more the defocus).

In some implementations, user accommodation is tracked in real-time. In an exemplary implementation, tracking the eye characteristic based on the comparison of the image of the portion of the retina with the representation of the eye is tracked at a same time (e.g., real-time) the image of the portion of the retina is received. For example, during the use of an application (e.g., an XR experience), eye tracking is performed in real-time, such as to initiate an action based on the real-time tracking of the user's eye(s) to enhance the XR experience.

Figure 7:
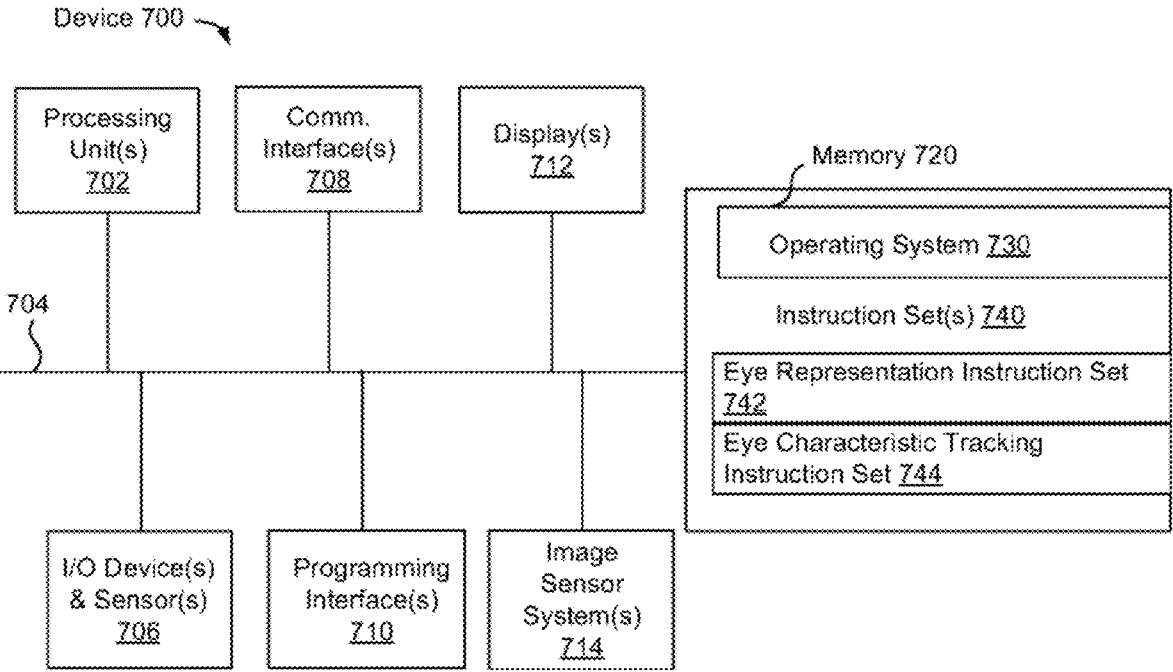
FIG. 7 is a block diagram illustrating device components of an exemplary device according to some implementations.

FIG. 7 is a block diagram of an example device 700. Device 700 illustrates an exemplary device configuration for device 10. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the device 10 includes one or more processing units 702 (e.g., microprocessors, ASICs, FPGAs, GPUs, CPUs, processing cores, and/or the like), one or more input/output (I/O) devices and sensors 706, one or more communication interfaces 708 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, SPI, 12C, and/ or the like type interface), one or more programming (e.g., I/O) interfaces 710, one or more displays 712, one or more interior and/or exterior facing image sensor systems 714, a memory 720, and one or more communication buses 704 for interconnecting these and various other components.

In some implementations, the one or more communication buses 704 include circuitry that interconnects and controls communications between system components. In some implementations, the one or more I/O devices and sensors 706 include at least one of an inertial measurement unit (IMU), an accelerometer, a magnetometer, a gyroscope, a thermometer, one or more physiological sensors (e.g., blood pressure monitor, heart rate monitor, blood oxygen sensor, blood glucose sensor, etc.), one or more microphones, one or more speakers, a haptics engine, one or more depth sensors (e.g., a structured light, a time-of-flight, or the like), and/or the like.

In some implementations, the one or more displays 712 are configured to present a view of a physical environment or a graphical environment to the user. In some implementations, the one or more displays 712 correspond to holographic, digital light processing (DLP), liquid-crystal display (LCD), liquid-crystal on silicon (LCoS), organic light-emitting field-effect transitory (OLET), organic light-emitting diode (OLED), surface-conduction electron-emitter display (SED), field-emission display (FED), quantum-dot light-emitting diode (QD-LED), micro-electromechanical system (MEMS), and/or the like display types. In some implementations, the one or more displays 712 correspond to diffractive, reflective, polarized, holographic, etc. waveguide displays. In one example, the device 10 includes a single display. In another example, the device 10 includes a display for each eye of the user.

In some implementations, the one or more image sensor systems 714 are configured to obtain image data that corresponds to at least a portion of the physical environment. For example, the one or more image sensor systems 714 include one or more RGB cameras (e.g., with a complimentary metal-oxide-semiconductor (CMOS) image sensor or a charge-coupled device (CCD) image sensor), monochrome cameras, IR cameras, depth cameras, event-based cameras, and/or the like. In various implementations, the one or more image sensor systems 714 further include illumination sources that emit light, such as a flash. In various implementations, the one or more image sensor systems 714 further include an on-camera image signal processor (ISP) configured to execute a plurality of processing operations on the image data.

The memory 720 includes high-speed random-access memory, such as DRAM, SRAM, DDR RAM, or other random-access solid-state memory devices. In some implementations, the memory 720 includes non-volatile memory, such as one or more magnetic disk storage devices, optical disk storage devices, flash memory devices, or other non-volatile solid-state storage devices. The memory 720 optionally includes one or more storage devices remotely located from the one or more processing units 702. The memory 720 includes a non-transitory computer readable storage medium.

In some implementations, the memory 720 or the non-transitory computer readable storage medium of the memory 720 stores an optional operating system 730 and one or more instruction set(s) 740. The operating system 730 includes procedures for handling various basic system services and for performing hardware dependent tasks. In some implementations, the instruction set(s) 740 include executable software defined by binary information stored in the form of electrical charge. In some implementations, the instruction set(s) 740 are software that is executable by the one or more processing units 702 to carry out one or more of the techniques described herein.

The instruction set(s) 740 include an eye representation instruction set 742 and an eye characteristic tracking instruction set 744. The instruction set(s) 740 may be embodied a single software executable or multiple software executables.

In some implementations, the eye representation instruction set 742 is executable by the processing unit(s) 702 to obtain a representation of the eye (e.g., an enrollment image/map) via a sensor. The eye representation instruction set 742 (e.g., eye representation instruction set 420 of FIG. 4) may be further configured to direct the user through an enrollment process as discussed herein. To these ends, in various implementations, the instruction includes instructions and/or logic therefor, and heuristics and metadata therefor.

In some implementations, the eye characteristic tracking instruction set 744 is executable by the processing unit(s) 702 to track a user's eye gaze characteristics (e.g., user accommodation distance via scaling and blurring) based on a comparison of the image of the portion of the retina with the representation of the eye using one or more of the techniques discussed herein or as otherwise may be appropriate. To these ends, in various implementations, the instruction includes instructions and/or logic therefor, and heuristics and metadata therefor.

Although the instruction set(s) 740 are shown as residing on a single device, it should be understood that in other implementations, any combination of the elements may be located in separate computing devices. Moreover, FIG. 7 is intended more as functional description of the various features which are present in a particular implementation as opposed to a structural schematic of the implementations described herein. As recognized by those of ordinary skill in the art, items shown separately could be combined and some items could be separated. The actual number of instructions sets and how features are allocated among them may vary from one implementation to another and may depend in part on the particular combination of hardware, software, and/or firmware chosen for a particular implementation.

Figure 8:
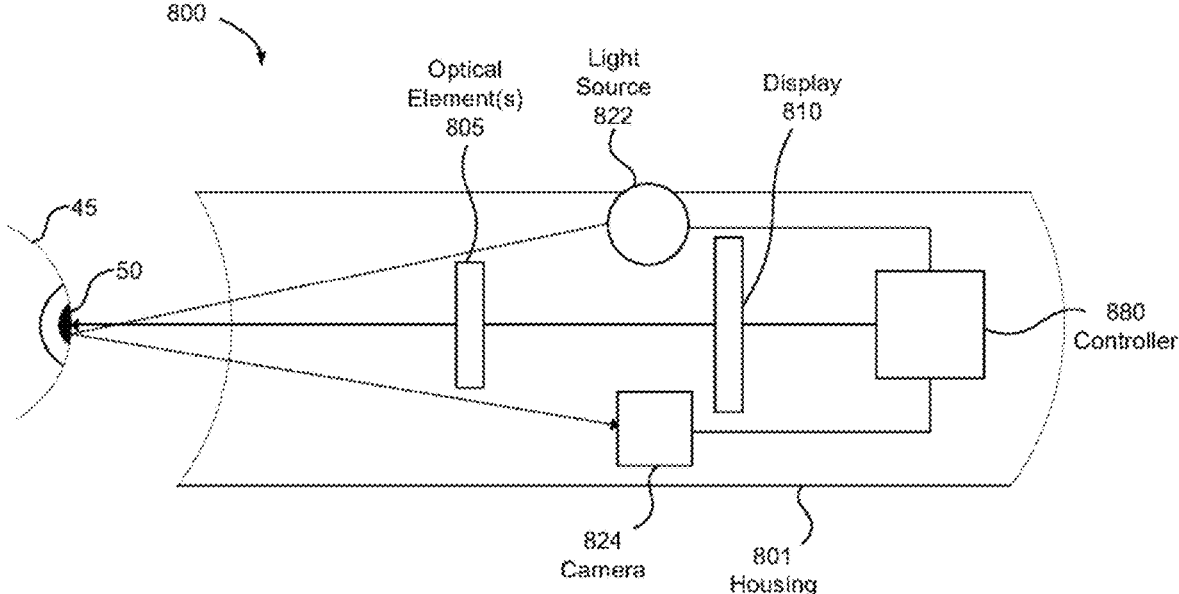
FIG. 8 is a block diagram of an example head-mounted device (HMD) in accordance with some implementations.

FIG. 8 illustrates a block diagram of an exemplary head-mounted device 800 in accordance with some implementations. The head-mounted device 800 includes a housing 801 (or enclosure) that houses various components of the head-mounted device 800. The housing 801 includes (or is coupled to) an eye pad (not shown) disposed at a proximal (to the user 25) end of the housing 801. In various implementations, the eye pad is a plastic or rubber piece that comfortably and snugly keeps the head-mounted device 800 in the proper position on the face of the user 25 (e.g., surrounding the eye of the user 25).

The housing 801 houses a display 810 that displays an image, emitting light towards or onto the eye of a user 25. In various implementations, the display 810 emits the light through an eyepiece having one or more optical elements 805 that refracts the light emitted by the display 810, making the display appear to the user 25 to be at a virtual distance farther than the actual distance from the eye to the display 810. For example, optical element(s) 805 may include one or more lenses, a waveguide, other diffraction optical elements (DOE), and the like. For the user 25 to be able to focus on the display 810, in various implementations, the virtual distance is at least greater than a minimum focal distance of the eye (e.g., 6 cm). Further, in order to provide a better user experience, in various implementations, the virtual distance is greater than 1 meter.

The housing 801 also houses a tracking system including one or more light sources 822, camera 824, and a controller 880. The one or more light sources 822 emit light onto the eye of the user 25 that reflects as a light pattern (e.g., a circle of glints) that can be detected by the camera 824. Based on the light pattern, the controller 880 can determine an eye tracking characteristic of the user 25. For example, the controller 880 can determine a gaze direction and/or a blinking state (eyes open or eyes closed) of the user 25. As another example, the controller 880 can determine a pupil center, a pupil size, or a point of regard. Thus, in various implementations, the light is emitted by the one or more light sources 822, reflects off the eye of the user 25, and is detected by the camera 824. In various implementations, the light from the eye of the user 25 is reflected off a hot mirror or passed through an eyepiece before reaching the camera 824.

The display 810 emits light in a first wavelength range and the one or more light sources 822 emit light in a second wavelength range. Similarly, the camera 824 detects light in the second wavelength range. In various implementations, the first wavelength range is a visible wavelength range (e.g., a wavelength range within the visible spectrum of approximately 400-800 nm) and the second wavelength range is a near-infrared wavelength range (e.g., a wavelength range within the near-infrared spectrum of approximately 700-1400 nm).

In various implementations, eye tracking (or, in particular, a determined gaze direction) is used to enable user interaction (e.g., the user 25 selects an option on the display 810 by looking at it), provide foveated rendering (e.g., present a higher resolution in an area of the display 810 the user 25 is looking at and a lower resolution elsewhere on the display 810), or correct distortions (e.g., for images to be provided on the display 810).

In various implementations, the one or more light sources 822 emit light towards the eye of the user 25 which reflects in the form of a plurality of glints.

In various implementations, the camera 824 is a frame/shutter-based camera that, at a particular point in time or multiple points in time at a frame rate, generates an image of the eye of the user 25. Each image includes a matrix of pixel values corresponding to pixels of the image which correspond to locations of a matrix of light sensors of the camera. In implementations, each image is used to measure or track pupil dilation by measuring a change of the pixel intensities associated with one or both of a user's pupils.

In various implementations, the camera 824 is an event camera including a plurality of light sensors (e.g., a matrix of light sensors) at a plurality of respective locations that, in response to a particular light sensor detecting a change in intensity of light, generates an event message indicating a particular location of the particular light sensor.

Returning to FIG. 1, a physical environment refers to a physical world that people can sense and/or interact with without aid of electronic devices. The physical environment may include physical features such as a physical surface or a physical object. For example, the physical environment corresponds to a physical park that includes physical trees, physical buildings, and physical people. People can directly sense and/or interact with the physical environment such as through sight, touch, hearing, taste, and smell. In contrast, an extended reality (XR) environment refers to a wholly or partially simulated environment that people sense and/or interact with via an electronic device. For example, the XR environment may include augmented reality (AR) content, mixed reality (MR) content, virtual reality (VR) content, and/or the like. With an XR system, a subset of a person's physical motions, or representations thereof, are tracked, and, in response, one or more characteristics of one or more virtual objects simulated in the XR environment are adjusted in a manner that comports with at least one law of physics. As one example, the XR system may detect head movement and, in response, adjust graphical content and an acoustic field presented to the person in a manner similar to how such views and sounds would change in a physical environment. As another example, the XR system may detect movement of the electronic device presenting the XR environment (e.g., a mobile phone, a tablet, a laptop, or the like) and, in response, adjust graphical content and an acoustic field presented to the person in a manner similar to how such views and sounds would change in a physical environment. In some situations (e.g., for accessibility reasons), the XR system may adjust characteristic(s) of graphical content in the XR environment in response to representations of physical motions (e.g., vocal commands).

There are many different types of electronic systems that enable a person to sense and/or interact with various XR environments. Examples include head mountable systems, projection-based systems, heads-up displays (HUDs), vehicle windshields having integrated display capability, windows having integrated display capability, displays formed as lenses designed to be placed on a person's eyes (e.g., similar to contact lenses), headphones/earphones, speaker arrays, input systems (e.g., wearable or handheld controllers with or without haptic feedback), smartphones, tablets, and desktop/laptop computers. A head mountable system may have one or more speaker(s) and an integrated opaque display. Alternatively, a head mountable system may be configured to accept an external opaque display (e.g., a smartphone). The head mountable system may incorporate one or more imaging sensors to capture images or video of the physical environment, and/or one or more microphones to capture audio of the physical environment. Rather than an opaque display, a head mountable system may have a transparent or translucent display. The transparent or translucent display may have a medium through which light representative of images is directed to a person's eyes. The display may utilize digital light projection, OLEDs, LEDs, uLEDs, liquid crystal on silicon, laser scanning light source, or any combination of these technologies. The medium may be an optical waveguide, a hologram medium, an optical combiner, an optical reflector, or any combination thereof. In some implementations, the transparent or translucent display may be configured to become opaque selectively. Projection-based systems may employ retinal projection technology that projects graphical images onto a person's retina. Projection systems also may be configured to project virtual objects into the physical environment, for example, as a hologram or on a physical surface.

It will be appreciated that the implementations described above are cited by way of example, and that the present invention is not limited to what has been particularly shown and described hereinabove. Rather, the scope includes both combinations and sub combinations of the various features described hereinabove, as well as variations and modifications thereof which would occur to persons skilled in the art upon reading the foregoing description and which are not disclosed in the prior art.

As described above, one aspect of the present technology is the gathering and use of physiological data to improve a user's experience of an electronic device with respect to interacting with electronic content. The present disclosure contemplates that in some instances, this gathered data may include personal information data that uniquely identifies a specific person or can be used to identify interests, traits, or tendencies of a specific person. Such personal information data can include physiological data, demographic data, location-based data, telephone numbers, email addresses, home addresses, device characteristics of personal devices, or any other personal information.

The present disclosure recognizes that the use of such personal information data, in the present technology, can be used to the benefit of users. For example, the personal information data can be used to improve interaction and control capabilities of an electronic device. Accordingly, use of such personal information data enables calculated control of the electronic device. Further, other uses for personal information data that benefit the user are also contemplated by the present disclosure.

The present disclosure further contemplates that the entities responsible for the collection, analysis, disclosure, transfer, storage, or other use of such personal information and/or physiological data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates implementations in which users selectively block the use of, or access to, personal information data. That is, the present disclosure contemplates that hardware or software elements can be provided to prevent or block access to such personal information data. For example, in the case of user-tailored content delivery services, the present technology can be configured to allow users to select to "opt in" or "opt out" of participation in the collection of personal information data during registration for services. In another example, users can select not to provide personal information data for targeted content delivery services. In yet another example, users can select to not provide personal information, but permit the transfer of anonymous information for the purpose of improving the functioning of the device.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences or settings based on non-personal information data or a bare minimum amount of personal information, such as the content being requested by the device associated with a user, other non-personal information available to the content delivery services, or publicly available information.

In some embodiments, data is stored using a public/private key system that only allows the owner of the data to decrypt the stored data. In some other implementations, the data may be stored anonymously (e.g., without identifying and/or personal information about the user, such as a legal name, username, time and location data, or the like). In this way, other users, hackers, or third parties cannot determine the identity of the user associated with the stored data. In some implementations, a user may access his or her stored data from a user device that is different than the one used to upload the stored data. In these instances, the user may be required to provide login credentials to access their stored data.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification discussions utilizing the terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general purpose computing apparatus to a specialized computing apparatus implementing one or more implementations of the present subject matter. Any suitable programming, scripting, or other type of language or combinations of languages may be used to implement the teachings contained herein in software to be used in programming or configuring a computing device.

Implementations of the methods disclosed herein may be performed in the operation of such computing devices. The order of the blocks presented in the examples above can be varied for example, blocks can be re-ordered, combined, or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or value beyond those recited. Headings, lists, and numbering included herein are for ease of explanation only and are not meant to be limiting.

It will also be understood that, although the terms "first," "second," etc. may be used herein to describe various objects, these objects should not be limited by these terms. These terms are only used to distinguish one object from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "or" as used herein refers to and encompasses any and all possible combinations of one or more of the associated listed items. It will be further understood that the terms "comprises" or "comprising," when used in this specification, specify the presence of stated features, integers, steps, operations, objects, or components, but do not preclude the presence or addition of one or more other features, integers, steps, operations, objects, components, or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description and summary of the invention are to be understood as being in every respect illustrative and exemplary, but not restrictive, and the scope of the invention disclosed herein is not to be determined only from the detailed description of illustrative implementations but according to the full breadth permitted by patent laws. It is to be understood that the implementations shown and described herein are only illustrative of the principles of the present invention and that various modification may be implemented by those skilled in the art without departing from the scope and spirit of the invention.

What is claimed is:

1. A method comprising:
at an electronic device having a processor:
    producing light that reflects off a retina of an eye;
    receiving an image of a portion of the retina from an image sensor, the image corresponding to a plurality of reflections of the light scattered from the retina of the eye;
    obtaining a representation of the eye corresponding to a first accommodative state, the representation representing at least some of the portion of the retina;
    tracking an eye characteristic based on a comparison of the image of the portion of the retina with the representation of the eye; and
    determining an accommodation of the eye based on estimating a blurring measure and estimating a geometric scaling factor between the image of the portion of the retina and the representation of the eye.

2. The method of claim 1, wherein the representation of the eye comprises a map of the at least some of the portion of the retina.

3. The method of claim 2, wherein generating the map of the at least some of the portion of the retina comprises:
    obtaining enrollment images of the eye of a user while the user (i) accommodates the eye to an enrollment depth, and (ii) scans through a gaze angle space representative of a defined field of view; and
    generating the map of the at least some of the portion of the retina based on combining at least a portion of two or more of the enrollment images of the eye.

4. The method of claim 1, wherein tracking the eye characteristic based on the comparison of the image of the portion of the retina with the representation of the eye comprises estimating a degree of defocus of a feature.

5. The method of claim 4, wherein estimating the degree of defocus of the feature is based on using focus pixels configured to measure focus for defocus estimation.

6. The method of claim 1, wherein tracking the eye characteristic based on the comparison of the image of the portion of the retina with the representation of the eye comprises:
    adjusting a focus position of a lens to increase an image sharpness metric; and
    determining an amount of defocus based on an amount of lens movement required to increase the image sharpness metric.

7. The method of claim 1, wherein tracking the eye characteristic based on the comparison of the image of the portion of the retina with the representation of the eye comprises:
    comparing a difference of a first feature width of the image of the portion of the retina with a second feature width of the representation of the eye to a threshold.

8. The method of claim 1, wherein tracking the eye characteristic based on the comparison of the image of the portion of the retina with the representation of the eye is tracked at a same time the image of the portion of the retina is received.

9. The method of claim 1, wherein the light is infrared (IR) light.

10. The method of claim 1, wherein the electronic device is a head-mounted device (HMD).

11. The method of claim 10, wherein the HMD comprises a waveguide.

12. A device comprising:
a non-transitory computer-readable storage medium; and
one or more processors coupled to the non-transitory computer-readable storage medium, wherein the non-transitory computer-readable storage medium comprises program instructions that, when executed on the one or more processors, cause the one or more processors to perform operations comprising:
    producing light that reflects off a retina of an eye;
    receiving an image of a portion of the retina from an image sensor, the image corresponding to a plurality of reflections of the light scattered from the retina of the eye;
    obtaining a representation of the eye corresponding to a first accommodative state, the representation representing at least some of the portion of the retina;
    tracking an eye characteristic based on a comparison of the image of the portion of the retina with the representation of the eye; and
    determining an accommodation of the eye based on estimating a blurring measure and estimating a geometric scaling factor between the image of the portion of the retina and the representation of the eye.

13. The device of claim 12, wherein the representation of the eye comprises a map of the at least some of the portion of the retina.

14. The device of claim 13, wherein generating the map of the at least some of the portion of the retina comprises:
    obtaining enrollment images of the eye of a user while the user (i) accommodates the eye to an enrollment depth, and (ii) scans through a gaze angle space representative of a defined field of view; and
    generating the map of the at least some of the portion of the retina based on combining at least a portion of two or more of the enrollment images of the eye.

15. The device of claim 12, wherein tracking the eye characteristic based on the comparison of the image of the portion of the retina with the representation of the eye comprises estimating a degree of defocus of a feature.

16. The device of claim 15, wherein estimating the degree of defocus of the feature is based on using focus pixels configured to measure focus for defocus estimation.

17. The device of claim 12, wherein tracking the eye characteristic based on the comparison of the image of the portion of the retina with the representation of the eye comprises:
    adjusting a focus position of a lens to increase an image sharpness metric; and
    determining an amount of defocus based on an amount of lens movement required to increase the image sharpness metric.

18. The device of claim 12, wherein tracking the eye characteristic based on the comparison of the image of the portion of the retina with the representation of the eye comprises:

comparing a difference of a first feature width of the image of the portion of the retina with a second feature width of the representation of the eye to a threshold.

19. The device of claim 12, wherein tracking the eye characteristic based on the comparison of the image of the portion of the retina with the representation of the eye is tracked at a same time the image of the portion of the retina is received.

20. The device of claim 12, wherein the light is infrared (IR) light.

21. The device of claim 12, wherein the device is a head-mounted device (HMD).

22. The device of claim 21, wherein the HMD comprises a waveguide.

23. A non-transitory computer-readable storage medium, storing program instructions executable on a device to perform operations comprising:

producing light that reflects off a retina of an eye;

receiving an image of a portion of the retina from an image sensor, the image corresponding to a plurality of reflections of the light scattered from the retina of the eye;

obtaining a representation of the eye corresponding to a first accommodative state, the representation representing at least some of the portion of the retina;

tracking an eye characteristic based on a comparison of the image of the portion of the retina with the representation of the eye; and determining an accommodation of the eye based on estimating a blurring measure and estimating a geometric scaling factor between the image of the portion of the retina and the representation of the eye.

24. The non-transitory computer-readable storage medium of claim 23, wherein the representation of the eye comprises a map of the at least some of the portion of the retina.

25. The non-transitory computer-readable storage medium of claim 24, wherein generating the map of the at least some of the portion of the retina comprises:

obtaining enrollment images of the eye of a user while the user (i) accommodates the eye to an enrollment depth, and (ii) scans through a gaze angle space representative of a defined field of view; and generating the map of the at least some of the portion of the retina based on combining at least a portion of two or more of the enrollment images of the eye.

26. The method of claim 1, wherein determining the accommodation of the eye is further based on mapping at least the estimated blurring measure and the estimated geometric scaling factor to an accommodation distance.

\* \* \* \* \*